United States Patent [19]
Ochoa Gomez et al.

[11] Patent Number: 5,268,079
[45] Date of Patent: Dec. 7, 1993

[54] PROCESS FOR THE ISOLATION AND PURIFICATION OF FREE ACIDS, STARTING FROM THEIR SALTS, BY ELECTRODIALYSIS

[75] Inventors: Jose R. Ochoa Gomez, Tres Cantos; Juan L. Martin Ramon; Asuncion de Diego Zori, both of Madrid, all of Spain

[73] Assignee: Monsanto Company, St. Louis, Mo.

[21] Appl. No.: 922,342

[22] Filed: Jul. 28, 1992

Related U.S. Application Data

[63] Continuation of Ser. No. 643,999, Jan. 18, 1991, abandoned.

[30] Foreign Application Priority Data

Jan. 18, 1990 [ES]  Spain ................................. 9000130
Oct. 4, 1990 [ES]  Spain ................................. 9002524

[51] Int. Cl.$^5$ ............................................. B01D 61/44
[52] U.S. Cl. ................................ 204/182.4; 204/182.6; 204/301
[58] Field of Search .................... 204/182.4, 182.6, 301

[56] References Cited

U.S. PATENT DOCUMENTS

| | | | |
|---|---|---|---|
| 2,865,822 | 12/1958 | Murphy | 204/72 |
| 3,330,749 | 7/1967 | Kuwata et al. | 204/182.6 |
| 3,926,759 | 12/1975 | Horn et al. | 204/182.4 |
| 3,964,985 | 6/1976 | Giuffrida | 204/182.6 |
| 4,375,393 | 3/1983 | Reiff et al. | 204/79 |
| 4,885,247 | 12/1989 | Datta | 435/139 |
| 4,909,916 | 3/1990 | Koberstein et al. | 204/182.6 |

*Primary Examiner*—John Niebling
*Assistant Examiner*—Arun S. Phasge
*Attorney, Agent, or Firm*—Frank D. Shearin

[57] ABSTRACT

Process for the isolation and purification of free acids, starting from their salts, by electrodialysis which involves the use of:

i) an electrolytic cell of four compartments, in which the two compartments adjacent to the two electrodes are separated from the central compartments by means of cationic membranes (2) and the central compartments are separated from one another by means of an anionic membrane (1); or, alternatively, ii) a module formed by an array of cells of 4 compartments separated from one another by alternating anionic membranes and cationic membranes.

By means of this process, the simultaneous presence of the isolated free acids and their salts in the same compartment is prevented, which increases their purity. A large number of acids and amino acids can be isolated and purified. In a preferred embodiment, the purification and isolation of IDA is described.

11 Claims, 2 Drawing Sheets

PROCESS FOR THE ISOLATION AND PURIFICATION OF FREE ACIDS, STARTING FROM THEIR SALTS, BY ELECTRODIALYSIS

This is a continuation of co-pending application Ser. No. 07/643,999 filed Jan. 1, 1991 abandoned.

FIELD OF THE INVENTION

The invention relates to a process for the isolation and purification of free acids from their salts by electrodialysis, which involves the use of
  i) an electrolytic cell of four compartments, in which the two compartments adjacent to both electrodes are separated from the central compartments by means of cationic membranes and the central compartments are separated from one another by means of an anionic membrane; or, alternatively,
  ii) a module formed by an array of cells of 4 compartments separated from one another by alternating anionic membranes and cationic membranes.

PRIOR ART

The use of electrodialysis for isolating and purifying free organic acids from their water-soluble salts has previously been described in the patent literature. Thus, for example, U.S. Pat. No. 2,921,005 describes the electrolytic conversion of salts of weak acids into said weak acids by using an electrolytic cell of 3 compartments, the central compartment of which is fed with a solution of the salt of the acid it is desired to purify. Both the cathodic and anodic compartments are separated from the central compartment by means of cationic membranes. When a potential difference is applied between the electrodes, both the protons of the anolyte solution and the cations of the solution of the central compartment migrate towards the cathode, while the anions remain in their compartments, since they cannot pass through the cationic membranes. In theory, a solution of the free acid in the central compartment is formed. However, in practice, this is extremely difficult to achieve, due to the difference in transport numbers of the protons and cations of the salt of the acid, which has the effect that at all times a solution of the free acid contaminated with the corresponding salt is present in the central compartment.

To get around this problem, U.S. Pat. No. 3,964,985 proposes the use of a cell of 4 compartments separated from one another by three cationic membranes. In this case, the solution containing the salt of the acid is fed by the two central compartments which recirculate it from the one nearest to the cathode to the one nearest to the anode. In this manner, it is possible to return a portion of the protons to the central compartment nearest to the anode, giving a solution of the free acid with a lower salt content. Despite being an improvement over the former, this process still has the disadvantage of being more complicated and cumbersome than the one proposed in this invention.

German Patent 3,405,522 proposes the use of an electrolytic cell composed of 3 compartments separated by two cationic membranes. The membranes used in this patent are perfluorinated olefin polymers which contain sulpho or carboxyl groups and styrene copolymers containing sulpho groups, while the procedure is very similar to that of U.S. Pat. No. 3,964,985.

Hitherto, an anionic membrane for separating the central compartments of an electrodialysis cell of 4 compartments was not used, so as to avoid the salt of the acid to be purified and the free acid being present in the same compartment, as a result of which the free acid obtained is not contaminated with the salt.

Accordingly, the present invention relates to a process for the isolation and purification of free acids from their water-soluble salts by electrodialysis by means of a cell of 4 compartments, whose two compartments adjacent to the two electrodes are separated from the central compartments by means of cationic membranes and whose central compartments are separated from one another by means of an anionic membrane, such as shown in FIG. 1. In this manner, from the beginning of electrolysis, the free acid form and the salt from which it originates are prevented from being present in the same compartment. This procedure is suitable for products of very high added value or small batches. For large batches, it is more appropriate to use a process whose scheme is shown in FIG. 2 and which is also provided by this invention.

Consequently, this patent application also applies to a process for the isolation and purification of free acids from their water-soluble salts by electrodialysis which involves the use of a module formed by an assembly of cells of 4 compartments like the one shown in FIG. 2.

In a preferred embodiment of the process of the invention, iminodiacetic acid (IDA) is isolated and purified, from its sodium salt. IDA is an essential intermediate in the synthesis of glyphosate, which is a broad-spectrum herbicide. Various methods for the synthesis of IDA have been claimed, for example, Spanish Patent 8,900,025, U.S. Pat. No. 3,153,688, U.S. Pat. No. 3,812,434, Japanese Patent 71/40,611 and Japanese Patent 78/77,009. The main problem with these processes does not lie in the synthesis itself, since yields of greater than 90% are obtained, but arises when an attempt is made to isolate and purify the IDA, from its sodium salt or another form, such as is usually obtained at the end of synthesis thereof.

DETAILED DESCRIPTION OF THE INVENTION

The invention relates to a process for the isolation and purification of free acids, starting from their salts, by electrodialysis by using
  i) an electrolytic cell of four compartments, in which the two compartments adjacent to the two electrodes are separated from the central compartments by means of cationic membranes and the central compartments are separated from one another by means of an anionic membrane; or, alternatively,
  ii) a module formed by a array of cells of 4 compartments separated from one another by alternating anionic membranes and cationic membranes.

It is to be understood that in the present description the term "anionic membrane" is used to indicate those membranes which have selective permeability and which allow the passage of anions but not of cations. Analogously, "cationic membrane" is used to indicate membranes which allow cations but not anions to pass through.

Figure 1:
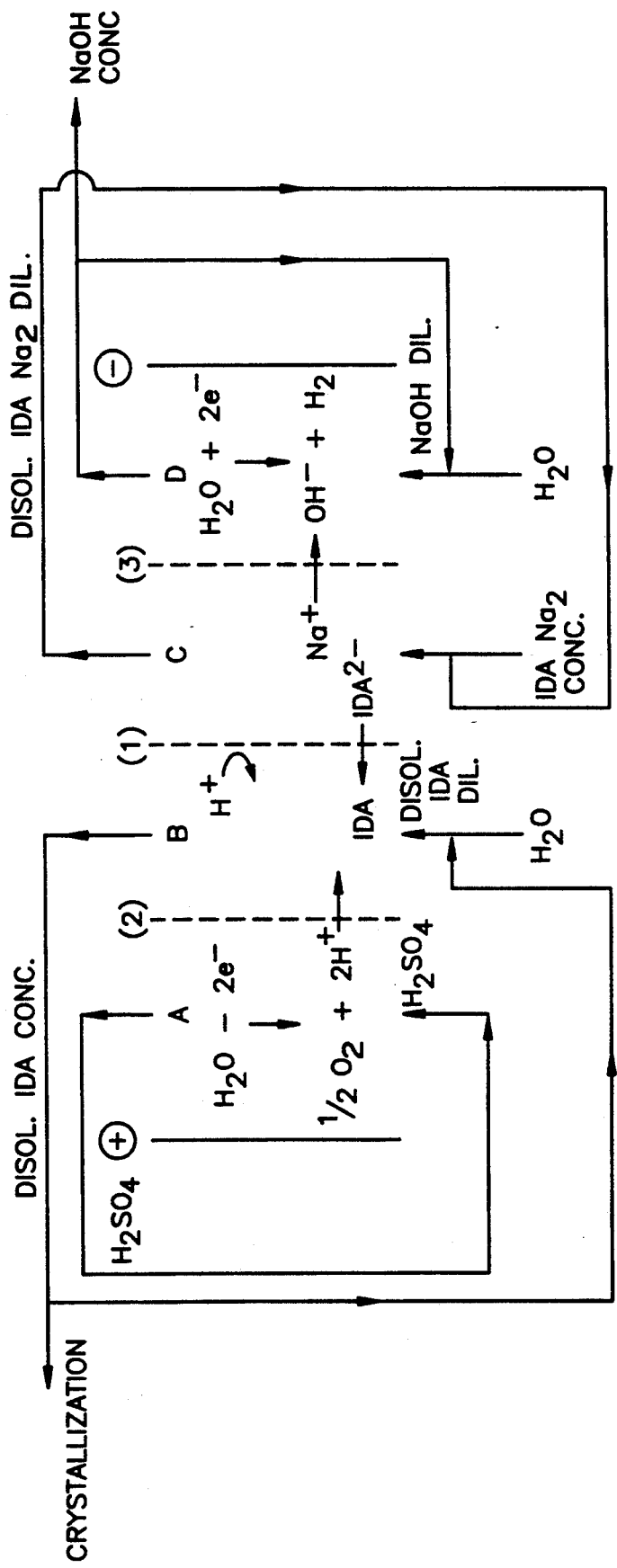
FIG. 1 shows a particular embodiment of the process of the invention applied to the isolation and purification of IDA, from its disodium salt, using a cell of 4 compartments.

In a first embodiment, the process for the isolation and purification of free acids of the invention can be carried out in an electrolytic cell of 4 compartments, such as the one shown in FIG. 1. This process generally comprises the following steps:

a) preparing an electrodialysis cell of 4 compartments, whose two compartments adjacent to the electrodes are separated from the central compartments by means of cationic membranes, while the two central compartments are separated from one another by an anionic membrane;

b) circulating:
a solution capable of generating protons in the compartment next to the anode;
a solution of a hydroxide in the compartment next to the cathode;
a solution of a water-soluble salt of the acid to be isolated and purified in the central compartment next to the cathode; and
water or an aqueous solution of the acid to be purified in the central compartment next to the anode;

c) applying a direct electric current between the electrodes so as to effect the migration of the different ions present in the electrolytic cell; and d) removing the aqueous solution of the pure and isolated free acid.

In general, the electrolytic cell of the present invention has 4 compartments (A, B, C and D). Compartment A (or anodic compartment) and compartment D (or cathodic compartment) are separated from the central compartments (B, C) by means of cationic membranes. On the other hand, the central compartments (B, C) are separated from one another by an anionic membrane. The use of this anionic membrane is essential and implies a clear difference from the processes known hitherto. The consequences of placing an anionic membrane between the central compartments will be detailed below in the description of what happens in the course of the migration of the ions present in the electrolytic cell when the electric current is applied.

The cationic and anionic membranes used in this process can be any of those usually commercially available. Thus, suitable cationic membranes are Nafion, Neosepta, Ionics, Selemion and anionic membranes are Neosepta, Ionics, Selemion, Tosflex, and the like.

The anodes which can be used are oxides of noble metals on a metal ($DSA_s$), platinum or lead oxide. The cathodes which can be used are any metals, preferably stainless steel.

As mentioned above, a solution capable of generating protons is recirculated in the compartment nearest to the anode (A). In general, it is preferable to use, as proton-generating solution, a solution of an inorganic acid, preferably sulphuric acid at a concentration of between 1% and 15% by weight.

An aqueous solution of a hydroxide is circulated in the compartment (D) nearest to the cathode. In particular, it is preferable for this hydroxide solution to have the same cation as the salt of the acid to be purified. In a preferred embodiment of the process of the invention, NaOH is recirculated, since IDA is purified, starting from its disodium salt.

Water or, in order to increase the initial conductivity and thus reduce the cell voltage, a dilute aqueous solution of the acid to be purified can be passed through the central compartment (B) nearest to the anode.

The aqueous solution of the salt of the acid which it is desired to isolate and purify is fed into the central compartment (C) nearest to the cathode. The concentration of the salt of the acid to be purified depends on its solubility at the operating temperature. In general, the starting salt of the acid to be isolated and purified is a water-soluble salt of alkali metal or alkaline earth metal.

Upon applying a potential difference between the electrodes of the cell, the protons originating from compartment A migrate to B, while the anions of the salt of the acid to be purified migrate from compartment C to B. In compartment B, the charges are neutralised, thus forming, from the very beginning, a solution of the free acid. The protons are retained in compartment B and cannot migrate to compartment C, since they face an ionic barrier, the anionic membrane, through which they cannot permeate. The cations from compartment C travel to D, where they react with the hydroxide ions generated as a result of the electrolytic reduction of water. At the same time, $H_2$ is generated at the cathode, which can be discharged into the atmosphere or collected, if desired, for later use. When $H_2SO_4$ is used as anolyte, $O_2$ is generated at the anode, which can be discharged into the atmosphere or collected, if desired, for later use. On the other hand, the hydroxide of the cation corresponding to the salt of the acid to be purified is generated in compartment D, which originates from compartment C, so that this hydroxide can be reused in the step in which the acid to be purified is synthesized.

Finally, the residue from compartment (B) goes to a unit for recovering the free acid either by crystallisation or precipitation.

This process can be carried out batchwise or continuously. Thus, the electrodialysis can be carried out until the free acid concentrations in compartment B and the hydroxide concentrations in D reach the desired value, this then being followed by discharging some of the material in order to remove a certain amount of solution so as to keep the volumes and concentrations of the solutions of compartments B and D constant. Fresh solution of the salt of the acid to be purified is being fed into compartment C as it is consumed. In this manner, a continuous process is obtained.

The current density suitable for carrying out this process can vary between 10 and 5,000 $A/m^2$, preferably between 500 and 2,000 $A/m^2$.

The electrodialysis temperature can be between ambient temperature and 60° C. It is preferable to work at a temperature of between 40° C. and 50° C., since this enables the heat generated by the Joule effect to be used for heating the solutions, thus reducing the heating-/cooling cost.

This process makes it possible to isolate and purify various types of acids, starting from their corresponding soluble salts. Thus, for example, the process is suitable for isolating and purifying IDA, phthalic acid, glycine, nitrilotriacetic, tartaric, acetic, ascorbic, maleic, acrylic, p-hydroxymandelic acid and derivatives, mandelic acid and derivatives, citric, oxalic, glyoxylic, phenylacetic and p-hydroxyphenylacetic acid, among others, with a degree of purity of 99.5%, a yield close to 100% and a current efficiency of between 80% and 95%.

This process is also suitable for isolating and purifying inorganic acids, starting from their water-soluble salts.

In what follows, a preferred embodiment of this process will be described, which applies to the isolation and purification of IDA and is based on FIG. 1.

As can be seen in FIG. 1, the electrolytic cell consists of 4 compartments. The central compartments B and C are separated by an anionic membrane (1). Compartments A (anodic compartment) and D (cathodic compartment) are separated from central compartments B and C by means of cationic membranes (2, 3). Different solutions originating from the corresponding tanks are circulated in each compartment by means of pumps (not shown). A solution of a mineral acid, preferably sulphuric acid, of a concentration of between 1 and 15% by weight is passed through compartment A. Initially, water is passed through compartment B or, in order to increase the initial conductivity and thus reduce the cell's potential, a solution of IDA in water can be passed through compartment B. The aqueous solution of the salt of IDA, in this particular case its disodium salt ($IDANa_2$) is fed into compartment C, and a solution of the hydroxide of the same cation as that of the salt in water (in this particular case NaOH) is fed into compartment D. When a potential difference is applied between the electrodes, the protons originating from compartment A migrate to B, while the IDA=(iminodiacetate) anions migrate from compartment C to B. The charges are neutralised in compartment B, resulting right from the beginning in a solution of the free acid (IDA). The protons cannot migrate to compartment C, since they face the anionic membrane through which they cannot permeate. The cations from compartment C migrate to D, where they react with the hydroxide ions generated as a result of the electrolytic reduction of water at the cathode. In compartment D, the hydroxide of the cation corresponding to the salt of the acid which originates from the reaction medium in which the IDA has been synthesised is furthermore generated, and it is therefore possible to reuse this hydroxide in the step in which IDA is synthesised.

In compartment B, free IDA is obtained, which is passed to a unit for recovering IDA either by crystallisation or by precipitation.

The concentration of the solution of the salt of iminodiacetic acid which feeds compartment C, depends on its solubility at the operating temperature and is in general between 5 and 40% by weight. The abovementioned anodes, cathodes and membranes as well as the operating conditions (current density, temperature, batchwise or continuous operation) are suitable for carrying out this particular embodiment of the process of the invention.

The advantages of the process of the present invention over other similar known processes are obvious, since from the very beginning free acid is obtained without the simultaneous presence of its salt at any time in the same compartment, which leads to higher purity of the acid obtained.

However, as mentioned above, this process is suitable for products of very high added value or small batches. For large batches, the investment to be made is higher, which is why it is more appropriate to carry out the process described below, whose scheme is shown in FIG. 2 and which is also provided by this patent application.

Figure 2:
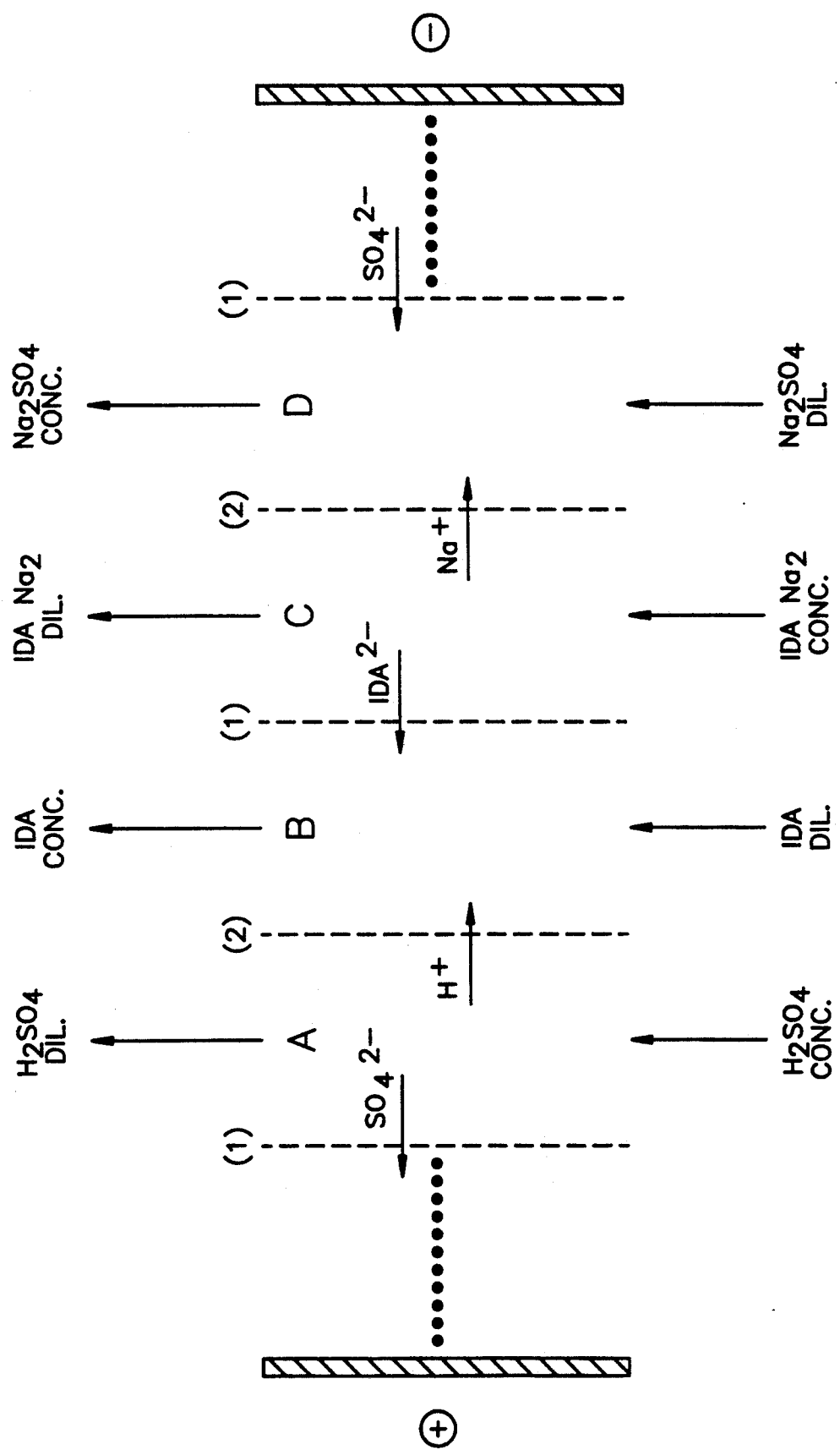
FIG. 2 shows a particular embodiment of the process of the invention applied to the isolation and purification of IDA, from its disodium salt, using a module formed by an array of cells of 4 compartments.

This process for the isolation and purification of free acids, starting from their salts, by electrodialysis, is carried out using a module formed by an array of cells of four compartments, which are assembled by stacking alternating anionic membranes and cationic membranes according to an arrangement shown in said FIG. 2. This process comprises the steps of:

a) preparing a compartmented electrodialysis cell by means of stacking, between two electrodes (anode and cathode), an array of alternating anionic membranes and cationic membranes;

b) circulating (see FIG. 2):
   a proton-generating solution in compartment (A');
   water or a dilute aqueous solution of the free acid to be isolated and purified in (B');
   an aqueous solution of a soluble salt of said acid to be isolated in (C'); and
   an aqueous solution of a salt in (D');

c) applying a direct electric current between the electrodes, as a result of which, after migration of the cations and anions, the desired free acid is formed in compartment (B') and the salt corresponding to the acid from compartment (A') is formed in compartment (D'); and d) removing the aqueous solution of the purified and isolated free acid obtained in compartment (B') for its recovery.

Both the anolyte and the catolyte (not shown in FIG. 2) are composed of an aqueous solution of a salt of the same composition in both cases. This salt preferably comprises the anion of the acid which is circulated in compartment (A') and the cation of the salt of the free acid to be isolated, which is circulated in compartment (C'). The compartments adjacent to the anode and the cathode, in which the anolyte and catolyte, respectively, (not shown) are circulated are composed of the corresponding electrode and a cationic membrane in both cases.

The anionic and cationic membranes can be any of those mentioned above. The anode and cathode which can be used are any of those mentioned above in connection with the process described above. In addition, graphite can also be used as the cathode.

A proton-generating solution is recirculated in compartment (A'), this solution generally being an aqueous solution of a mineral acid, preferably sulphuric acid, of a concentration of between 0.5% and 20% by weight. Other inorganic acids (HCl, $HNO_3$) can also be used.

Water or a dilute aqueous solution of the acid to be isolated and purified can be circulated in compartment (B').

The aqueous solution of the soluble salt of the acid to be isolated and purified is circulated in compartment (C'). The concentration of this salt depends on its solubility at the operating temperature. In general, the starting salt of the acid to be isolated and purified is a salt of an alkali metal, although it can also be a water-soluble salt of an alkaline earth metal.

An aqueous solution of a salt, in general composed of the same anion as that of the acid which is circulated in compartment (A') and by the same cation as that of the salt of the acid to be isolated and purified, is circulated in compartment (D'). Accordingly, in a preferred embodiment of the invention, the acid which is circulated in (A') is sulphuric acid, the salt of the acid to be isolated is the sodium or disodium salt and therefore the salt which is circulated in (D') is sodium sulphate.

The current density can be between 100 and 1,000 A/m², preferably between 200 and 500 A/m². This process for the isolation and purification can be carried out at a temperature of between 15° C. and 60° C., preferably between 30° C. and 50° C.

When applying a potential difference between the electrodes of the cell, the protons originating from compartment A' migrate to B', while the anions of the salt of the acid to be purified migrate from compartment C' to B'. The charges are neutralised in compartment B', forming from the very beginning a solution of the free acid. The protons are retained in compartment B' and cannot migrate to compartment C', since they face an ionic barrier, the anionic membrane, through which they cannot permeate. The cations from compartment C' travel to D', where they react with the anions from the other adjacent module, resulting in the formation of the corresponding salt. On the other hand, the salt of the acid which is circulated in A' with the cation corresponding to the salt of the acid to be purified is generated in compartment D', so that this salt can be reused in successive electrodialysis cycles or can be removed if it is a product of interest. In a preferred embodiment, the salt obtained is sodium sulphate, a product of commercial interest.

Finally, the residue from compartment B' can go to a unit for recovering the free acid either by crystallisation or by precipitation, or by another conventional technique.

This process can be carried out batchwise or continuously. Thus, electrodialysis can be carried out until the concentrations of the free acid in compartment B' and of the salt in D' reach the desired value, followed by discharging some of the material in order to remove a certain amount of solution to keep the volumes and concentrations of the solutions of compartments B' and D' constant. Fresh solution of the salt of the acid to be purified is fed into compartment C' as it is consumed. In this manner, a continuous process is maintained.

This process makes it possible to purify the above-mentioned organic acids, starting from their corresponding salts, with a degree of purity of 99.5%, a yield close to 100% and a current efficiency of between 80% and 95%.

Additionally, this process is also suitable for isolating and purifying inorganic acids, starting from their water-soluble salts.

A particular embodiment of this process for isolating and purifying acids is described below, applied to the disodium salt of iminodiacetic acid, so as to obtain isolated and pure IDA. In what follows, this particular embodiment will be described by referring to the scheme shown in FIG. 2.

As can be seen in said FIG. 2, a series of alternating anionic membranes (1) and cationic membranes (2) are arranged between 2 electrodes in such a manner that 4 compartments (A', B', C' and D') are delimited. A solution of concentrated $H_2SO_4$ is then fed into compartment (A'), a dilute aqueous solution of IDA into (B'), an aqueous solution of the disodium salt of IDA (IDANa$_2$) into (C') and a dilute $Na_2SO_4$ solution into (D'). Both the anolyte and catolyte are composed of an aqueous solution of the same composition, namely of $Na_2SO_4$. When a potential difference is applied to the electrodes, the anions ($IDA^{2-}$, $SO_4^{2-}$) migrate towards the anode through the anionic membranes and the cations ($Na^+$, $H^+$) migrate to the cathode through the cationic membranes in such a manner that, due to the arrangement of the membranes in compartment (B'), the $IDA^{2-}$ ions from compartment (C') react with the $H^+$ from compartment (A'), forming IDA of high purity. Likewise, by a similar process, $Na_2SO_4$ of high purity is formed in compartment (D'). This process makes it possible to obtain IDA with a purity of greater than 99% and a current efficiency of between 80 and 90%, when working at a current density of between 100 and 500 A/m² and at a temperature between 15° C. and 60° C. Typical operating concentrations, it not being possible to consider the remaining ones as excluded, are (0.5-20)% by weight for $H_2SO_4$, (5-55) g/l for IDA, (10-25)% by weight for the disodium salt of IDA and (5-25)% for $Na_2SO_4$. This isolation and purification process has the enormous advantage of achieving 100% recovery of the synthesised iminodiacetic acid in a purity of greater than 99% and a low consumption of energy, which is typically between 0.6 and 1.5 kWh/kg, additionally producing an industrially useful by-product, $Na_2SO_4$.

This process produces the free acid without its salt being simultaneously present at any time in the same compartment, which leads to greater purity of the acid obtained.

The examples which follow illustrate the process of the present invention and should not be considered as limiting it. Specific details have been given therein for the particular case of the isolation and purification of IDA, although the teachings of the present invention can obviously be applied to the isolation and purification of other acids, starting from their water-soluble salts, by electrodialysis, simply by changing the starting salt of the acid and optimising the operating conditions in each case.

EXAMPLES

Example 1

A cell of 4 compartments like that described in FIG. 1 having an effective electrode surface area of 20 cm² is used. Iridium oxide on titanium is used as the anode and stainless steel as the cathode. The electrodes and the three membranes are separated from one another by means of plastic frames. The spacing between the electrodes is 5 cm. The cationic membrane next to the anode is Nafion 324. The central anionic membrane is Selemion AMV, and the cationic membrane next to the cathode is Nafion 901. An aqueous 5% by weight sulphuric acid solution is circulated in compartment A. In compartment B, 300 cc of water. In compartment C, 300 cc (334 g) of a 20% by weight aqueous solution of the disodium salt of iminodiacetic acid (0.377 mol) and in D, 300 cc of 5% by weight NaOH. By means of a direct-current source, a current of 1 ampere intensity (current density 500 A/m²) is passed across the electrodes for 14 hours. The temperature is maintained at 30° C. At the end of said time, 340 cc of an aqueous solution of free IDA, which is already beginning to crystallise, are obtained in compartment B. Concentration by evaporation and precipitation with acetone gives, after drying, 34 g of IDA having a purity of 99.5% (current efficiency 98%). 183 cc of a solution containing 21.5 g of the disodium salt of IDA remain in compartment C. The mass balance is 100%. 320 cc of a 10.5% by weight NaOH solution are obtained in compartment D.

The average cell voltage was 11.5 volts, which corresponds to an energy consumption of 4.8 kWh/kg.

Example 2

The procedure of Example 1 is repeated, but at a current density of 1,000 A/m$^2$. The average cell voltage was 29 volts. The electrodialysis time was 4 hours 24 minutes, and the current efficiency 95%. 99.2% pure iminodiacetic acid was obtained. The specific energy consumption was 14 kWh/kg.

Example 3

The procedure of Example 1 is repeated, but at a current density of 1,500 A/m$^2$, at a temperature of 50° C. and at a concentration of the disodium salt in compartment C of 25%. The electrodialysis time was 4 hours 55 minutes. The average cell voltage was 24.8 volts, and 98.8% pure IDA was obtained with a current efficiency of 95%. The specific energy consumption was 10.4 kWh/kg.

Example 4

The procedure of the previous example was repeated, but at a current density of 2,000 A/m$^2$ and at a temperature of 59° C. The electrodialysis time was 5 hours 49 minutes. The average cell voltage was 30 volts. The current efficiency was 93% and 99% pure IDA was obtained. The specific energy consumption was 13 kWh/kg.

Example 5

The procedure of the previous example was repeated, except that the spacing between the electrodes was modified, which in this example was 1.2 cm. The average cell voltage was 15 volts. The purity of the IDA obtained was 99.5%. The current efficiency was 98% and the specific energy consumption 6.31 kWh/kg.

Example 6

An electrodialysis module composed of 12 cells of 4 compartments, as shown in FIG. 2, was used. The anode consisted of Pt/Ti and the cathode of stainless steel. The spacing between the membranes was 0.8 mm. The anionic membranes were of the Neosepta AM 1 type and the cationic membranes of the Neosepta CM 1 type. The active surface area of each membrane was 0.05 m$^2$, such that the effective total surface area was 0.6 m$^2$ and the total membrane surface 2.4 m$^2$. Initially, the following aqueous solutions originating from 5 40-liter tanks were circulated through the electrodialysis module by means of 5 magnetic displacement pumps.

a) a 5% sodium sulphate solution in the anodic and cathodic compartments (not shown in the figure);
b) a 1% sulphuric acid solution in compartment A';
c) a 25 g/l iminoacetic acid solution in compartment B';
d) a 10% solution of disodium salt of iminodiacetic acid in compartment C'; and
e) a 3.5% sodium sulphate solution in compartment D'.

The water used was deionised water. Subsequently and after adjusting the temperature of all solutions to 39° C., a direct current of 12.5 amperes was applied to the two electrodes, so that the current density was 250 A/m$^2$.

From this moment on, the operating mode was as follows:

I) 96% H$_2$SO$_4$ and deionised water was added at regular intervals to compartment A' to keep its concentration constant at around 1%. The addition was regulated in such a manner that the pH of the solution was always between 0.8 and 1;

II) the IDA concentration in compartment B' was allowed to reach 45 g/l. At this moment, 88% of the volume present was removed and conveyed to a crystalliser, where the IDA was subsequently crystallised at 5° C. After filtration, the filtrate was returned to the tank corresponding to compartment B,, so that the IDA concentration was again of the order of 25-28 g/l, and the operation described was repeated when its concentration again reached 45 g/l. The filtered IDA product was dried at 80° C., ground and bottled.

A portion of the solution (0.9 l/h×m$^2$) was removed in order to evaporate off the water and compensate for the increase in volume produced by electroosmosis;

III) disodium salt of IDA and water were added to compartment C' at regular intervals in order to keep its concentration constant at around 10%. The addition of Na$_2$ IDA and water was controlled by monitoring the density of the solution as a function of time;

IV) when the Na$_2$SO$_4$ concentration in compartment D' had reached 15%, 80% of its volume was removed and a sufficient amount of water was added to reduce the Na$_2$SO$_4$ concentration to a value of between 3.5% and 6%.

Following the described procedure, the electrodialyser was kept running for 1,000 hours, at the end of which 336.8 kg of IDA were obtained; thus, the current efficiency was 90.5% and the recovery (material yield) 99.9%. The productivity was 0.561 kg/h×m$^2$. The average voltage was kept constant at around 17.5 volts, so that the specific energy consumption was 0.65 kWh/kg. The H$_2$SO$_4$ consumption was 0.93 kg/kg of IDA.

The purity of IDA was analysed by HPLC, taking 28 samples spread over the entire course of the operation. Statistical analysis of the results obtained indicated that the purity of the final product was (99.2±0.14)% for a confidence interval of 95%.

Example 7

The procedure in this case was as indicated in Example 6, but at a current density of 500 A/m$^2$. The operation was maintained for 120 hours. 78.6 kg of IDA were produced. The current efficiency was 88% and the recovery 99.9%. The productivity was 1.09 kg/h×m$^2$. The average voltage was kept constant at around 40 volts. The specific energy consumption was 0.77 kWh/kg of IDA. The purity of the product obtained was 99.5%.

Example 8

The procedure was as indicated in Example 6 but the temperature was 30° C. The operating time was 120 hours. The productivity and current efficiency as well as the purity of the product obtained were the same as those obtained in Example 6. The average voltage was 19 volts and the specific energy consumption 0.71 kWh/kg.

Having described the subject-matter of the present invention, it is declared that the essential aspect of the inventions are as mentioned in the following claims:

We claim:

1. A process for the isolation and purification of carboxylic and aminocarboxylic acids starting from their water-soluble salts, by electrodialysis, which comprises:
   a. preparing an electrodialysis cell containing an anode and a cathode and four compartments formed by a central anionic membrane and an anionic membrane near the anode and another anionic membrane near the cathode, and a cationic membrane between the central anionic membrane and the anionic membrane near the anode to form a first compartment between the anionic membrane nearest the anode and the cationic membrane, and a second compartment between the cationic membrane nearest the anode and the central anionic membrane, and another cationic membrane between the central anionic membrane and the anionic membrane near the cathode to form a third compartment between the central anionic membrane and the cationic membrane nearer the cathode, and a fourth compartment between the cationic membrane and the anionic membrane nearer the cathode;
   b. introducing into
      the first compartment, a concentrated solution of mineral acid;
      the second compartment, a diluted aqueous solution of the carboxylic or aminocarboxylic acid to be purified;
      the third compartment, an aqueous solution of the alkali metal or alkaline earth salt of the carboxylic or aminocarboxylic acid to be purified; and
      the fourth compartment, an aqueous solution of a salt formed by an anion which is the same as that of the acid circulated through the first compartment and by a cation which is the same as that of the salt circulated through the third compartment;
   c. applying a direct electric current between the anode and the cathode whereby hydrogen ions from the first compartment migrate to the second compartment and anions from the third compartment migrate to the second compartment to form the purified acid in the second compartment; and
   d. recovering the purified acid.

2. The process according to claim 1 wherein the salt of the acid to be purified is introduced initially at a concentration which is a function of its solubility at the temperature at which the electrodialysis is performed.

3. The process according to claim 2, wherein the electrodialysis is performed at a temperature between 30° C. and 50° C.

4. The process according to claim 1, wherein the salt in the fourth compartment is sodium sulfate.

5. The process according to claim 1, wherein the acid obtained in iminodiacetic acid.

6. The process according to claim 1, wherein the purified acid is selected from the group consisting of glycine, oxalic, glyoxylic, p-hydroxymandelic, phenylacetic, and p-hydroxyphenylacetic acid.

7. A process for the isolation and purification of iminodiacetic acid, starting from its water-soluble salts, by electrodialysis, which comprises:
   a. preparing an electrodialysis cell containing an anode and a cathode and four compartments formed by a central anionic membrane and an anionic membrane near the anode and another anionic membrane near the cathode, and a cationic membrane between the central anionic membrane and the anionic membrane near the anode to form a first compartment between the anionic membrane nearest the anode and the cationic membrane, and a second compartment between the cationic membrane nearest the anode and the central anionic membrane, and another cationic membrane between the central anionic membrane and the anionic membrane near the cathode to form a third compartment between the central anionic membrane and the cationic membrane nearer the cathode, and a fourth compartment between the cationic membrane and the anionic membrane nearer the cathode;
   b. circulating through:
      the first compartment, an aqueous solution of a mineral acid;
      the second compartment, water or a diluted aqueous solution of iminodiacetic acid;
      the third compartment, an aqueous solution of disodium salt of iminodiacetic acid; and
      the fourth compartment, an aqueous solution of a salt;
   c. applying a direct electric current between the anode and the cathode whereby hydrogen ions from the first compartment migrate to the second compartment and iminodiacetate anions form the third compartment migrate to second compartment, and purified iminodiacetic acid is formed in the second compartment without being in contact with the solution of its salt; and
   d. removing the purified iminodiacetic acid obtained.

8. The process according to claim 7 wherein the disodium salt of iminodiacetic acid is introduced initially at a concentration which is a function of its solubility at the temperature at which the electrodialysis is performed.

9. The process according to claim 8 wherein the electrodialysis is performed at a temperature between 30+ C. and 50° C.

10. The process according to claim 7 wherein the salt which circulates through the fourth compartment is formed by an anion which is the same as that of the acid circulated through the first compartment, and the cation is sodium.

11. The process according to claim 10 wherein the salt which circulates through the fourth compartment is sodium sulfate.

* * * * *